(12) United States Patent
Bennette et al.

(10) Patent No.: US 11,743,986 B2
(45) Date of Patent: Aug. 29, 2023

(54) LUMINAIRE AND SYSTEM THAT USES THE SAME

(71) Applicant: Electronic Theatre Controls, Inc., Middleton, WI (US)

(72) Inventors: Adam Bennette, London (GB); David J. Cahalane, Dane, WI (US); Andrew Slade, Middleton, WI (US)

(73) Assignee: Electronic Theatre Controls, Inc., Middleton, WI (US)

( * ) Notice: Subject to any disclaimer, the term of this patent is extended or adjusted under 35 U.S.C. 154(b) by 77 days.

(21) Appl. No.: 17/320,867

(22) Filed: May 14, 2021

(65) Prior Publication Data

US 2021/0360757 A1   Nov. 18, 2021

Related U.S. Application Data

(60) Provisional application No. 63/026,453, filed on May 18, 2020.

(51) Int. Cl.
 H05B 45/10 (2020.01)
 H05B 45/30 (2020.01)
 (Continued)

(52) U.S. Cl.
 CPC ............... H05B 45/30 (2020.01); A61L 2/10 (2013.01); H05B 45/10 (2020.01);
 (Continued)

(58) Field of Classification Search
 CPC ........ H05B 45/10; H05B 45/20; H05B 45/30; H05B 45/375; H05B 45/52; H05B 45/54;
 (Continued)

(56) References Cited

U.S. PATENT DOCUMENTS 9,402,288 B2 *   7/2016  Xu ..................... H05B 45/37
10,136,485 B1 *  11/2018 Coetzee ............. H05B 45/42
(Continued)

FOREIGN PATENT DOCUMENTS

DE   202015100733 U1   5/2016
JP   2019140347 A   *   8/2019
JP   2019140347 A       8/2019

OTHER PUBLICATIONS

Examination Report issued from the Germany Patent Office for related Application No. 102021112912.5 dated Feb. 24, 2022 (7 pages including the Statement of Relevance).
(Continued)

*Primary Examiner* — Thai Pham
(74) *Attorney, Agent, or Firm* — Michael Best & Friedrich LLP (57) ABSTRACT

A luminaire including an input driven in a first polarity and a second polarity reversed from the first polarity, a first light source coupled to the input and adapted to generate visible light within a first wavelength range at a first intensity when the input is driven in the first polarity and adapted to generate visible light within the first wavelength range at a second intensity less than the first intensity when the input is driven in the second polarity, and a second light source coupled to the input and adapted to generate light within a second wavelength range, different than first wave length range, at a third intensity when the input is driven in the second polarity and adapted to generate light within the second wavelength range at a fourth intensity less than the third intensity when the input is driven in the first polarity.

21 Claims, 8 Drawing Sheets

(51) Int. Cl.
*A61L 2/10* (2006.01)
*H05B 45/375* (2020.01)

(52) U.S. Cl.
CPC ........ *A61L 2202/11* (2013.01); *A61L 2202/14* (2013.01); *H05B 45/375* (2020.01)

(58) Field of Classification Search
CPC ......... H05B 47/10; H05B 47/195; A61L 2/10; A61L 2/0047; A61L 2/0052; A61L 2202/11; A61L 2202/14
See application file for complete search history.

(56) References Cited

U.S. PATENT DOCUMENTS

| | | | |
|---|---|---|---|
| 10,363,327 B2 | 7/2019 | Liao et al. | |
| 10,667,362 B1* | 5/2020 | Coetzee | H05B 45/39 |
| 10,806,002 B2* | 10/2020 | Herrmann | H05B 45/325 |
| 2007/0262920 A1* | 11/2007 | Werner | H05B 45/46 |
| | | | 345/46 |
| 2010/0066258 A1 | 3/2010 | Yasuda | |
| 2010/0244724 A1* | 9/2010 | Jacobs | H05B 45/32 |
| | | | 315/253 |
| 2012/0229037 A1* | 9/2012 | Moskowitz | H05B 45/52 |
| | | | 315/192 |
| 2012/0280635 A1 | 11/2012 | Lu et al. | |
| 2012/0319600 A1* | 12/2012 | Ruxton | H05B 45/44 |
| | | | 315/186 |
| 2013/0009560 A1 | 1/2013 | Takeda et al. | |
| 2013/0106305 A1 | 5/2013 | Whitaker et al. | |
| 2014/0333219 A1* | 11/2014 | Zijlstra | H05B 45/39 |
| | | | 315/192 |
| 2017/0347411 A1* | 11/2017 | Gallo | H05B 45/44 |
| 2019/0186724 A1 | 6/2019 | Xie | |
| 2019/0306943 A1 | 10/2019 | Miskin | |

OTHER PUBLICATIONS

Search Report issued from the United Kingdom Patent Office for related Application No. GB2107066.9 dated Nov. 4, 2021, (4 Pages).

* cited by examiner

LUMINAIRE AND SYSTEM THAT USES THE SAME

CROSS-REFERENCE TO RELATED APPLICATIONS

This application claims priority to co-pending U.S. Provisional Patent Application No. 63/026,453 filed on May 18, 2020, the contents of which is incorporated herein by reference.

FIELD OF THE DISCLOSURE

The present disclosure relates to a luminaire for sanitizing a space or objects. The present disclosure also relates to a luminaire for alternatively illuminating a space with a first light source and a second light source. The present disclosure is further directed to a system that uses the luminaires.

SUMMARY

In one embodiment, a luminaire includes a voltage input capable of being driven in either a first polarity (e.g., straight polarity) or a second polarity (e.g., reverse polarity) reversed from the first polarity, a first light source (e.g., an illuminating light, such as white LEDs) coupled to the voltage input, and a second light source (e.g., a sanitizing light, such as UV-C LEDs) coupled to the voltage input. The first light source is adapted to generate visible light at a first intensity when the voltage input is driven with the first polarity and adapted to generate visible light at a second intensity (e.g., zero) less than the first intensity when the voltage input is driven with the second polarity. The second light source is adapted to generate non-visible light at a third intensity when the voltage input is driven with the second polarity and adapted to generate non-visible light (e.g., UV light) at a fourth intensity (e.g., zero) less than the third intensity when the voltage input is driven with the first polarity.

In another embodiment, a luminaire includes an input capable of being driven in a first polarity and a second polarity reversed from the first polarity, a first light source coupled to the input, and a second light source coupled to the input. The first light source is adapted to generate visible light within a first wavelength range at a first intensity when the input is driven in the first polarity and adapted to generate visible light within the first wavelength range at a second intensity less than the first intensity when the input is driven in the second polarity. The second light source is adapted to generate light within a second wavelength range at a third intensity when the input is driven in the second polarity and adapted to generate light within the second wavelength range at a fourth intensity less than the third intensity when the input is driven in the first polarity. The second wavelength range is different than the first wavelength range.

In another embodiment, a system includes a power source and a controller coupled to the power source and capable of switching a polarity of the power source from a first polarity to a second polarity reversed from the first polarity. The system further includes an input in communication with the power source via the controller, a first light source coupled to the input, and a second light source coupled to the input. The first light source is adapted to generate visible within a first wavelength range at a first intensity when the input is driven in the first polarity and adapted to generate visible light within the first wavelength range at a second intensity less than the first intensity when the input is driven in the second polarity. The second light source is adapted to generate light within a second wavelength range at a third intensity when the input is driven in the second polarity and adapted to generate light within the second wavelength range at a fourth intensity less than the third intensity when the input is driven in the first polarity. The second wavelength range is different than the first wavelength range.

In another embodiment, a system includes a power source, a controller coupled to the power source and capable of switching a polarity of the power source from a first polarity to a second polarity reversed from the first polarity, and a luminaire. The controller is a constant current driver. The luminaire includes an input in communication with the power source via the controller, a first light source coupled to the input, and a second light source coupled to the input. The first light source is adapted to generate visible white light at a first intensity when the input is driven in the first polarity and adapted to generate visible white light at a second intensity less than the first intensity when the input is driven in the second polarity. The second light source is adapted to generate non-visible light and visible non-white light at a third intensity when the input is driven in the second polarity. The second light source is adapted to generate non-visible light and visible non-white light at a fourth intensity less than the third intensity when the input is driven in the first polarity.

One way to accomplish the above is to provide the luminaire with a first current steering diode and a second current steering diode. The first current steering diode may be arranged to provide current to the first light source when the voltage input has the first polarity and inhibit current to the first light source when the voltage input has the second polarity. The second current steering diode may be arranged to provide current to the second light source when the voltage input has the second polarity and inhibit current to the second light source when the voltage input has the first polarity.

The above-described luminaire can be used with a single power source, a single controller coupled to the power source, and a single associated wiring, thus avoiding the need for multiple input wiring systems. The controller is capable of switching the polarity of the power source from the first polarity to the second polarity.

Other aspects of the disclosure will become apparent by consideration of the detailed description and accompanying drawings.

DETAILED DESCRIPTION

Before any aspects of the disclosure are explained in detail, it is to be understood that the disclosure is not limited in its application to the details of construction and the arrangement of components set forth in the following description or illustrated in the following drawings. The disclosure is capable of supporting other aspects and being practiced or being carried out in various ways. Also, it is to be understood that the phraseology and terminology used herein is for the purpose of description and should not be regarded as limiting.

Figure 1A:
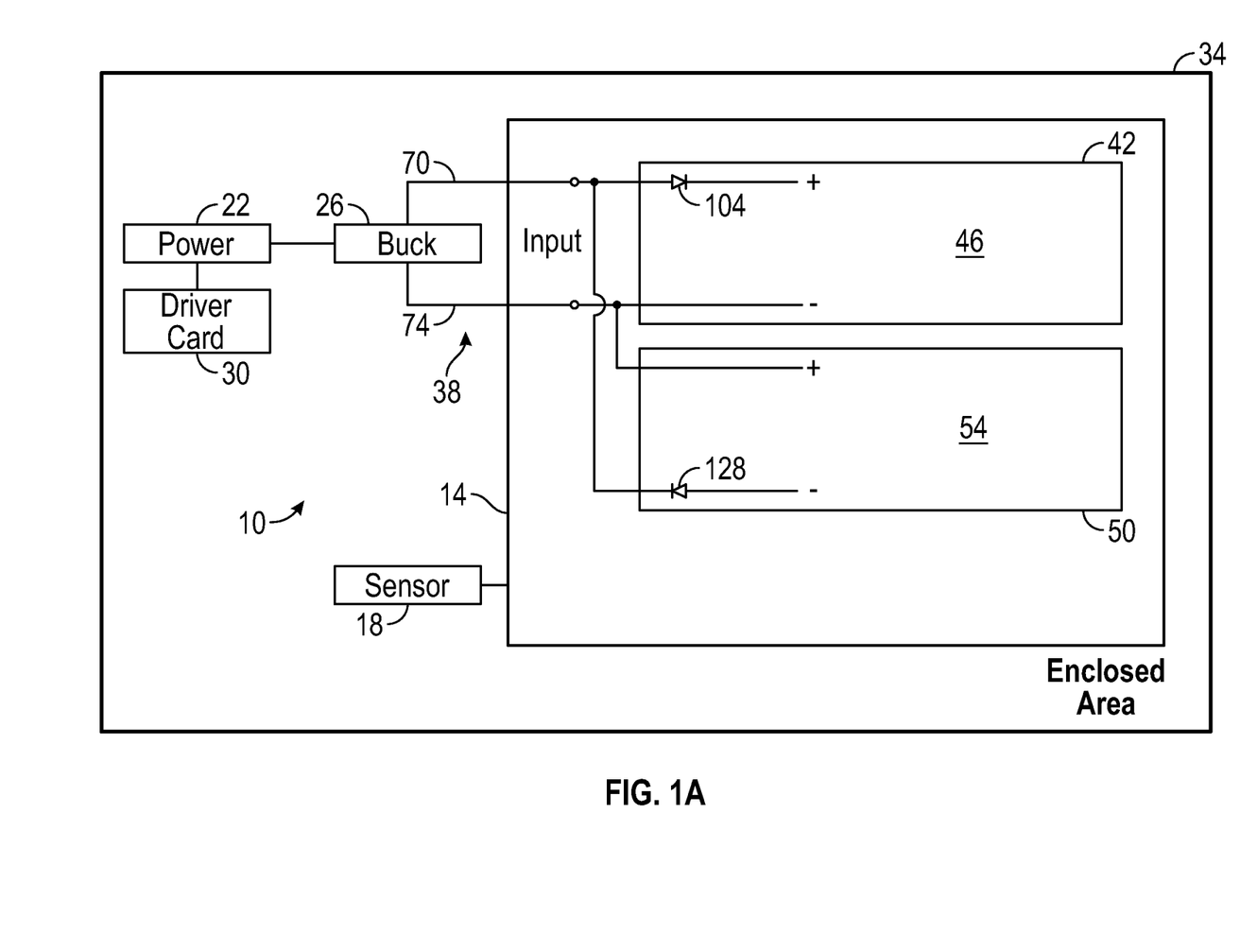
FIG. 1A is a schematic of a system according to one embodiment including a remote driver having one configuration and including a luminaire having a first light source and a second light source.
Figure 4A:
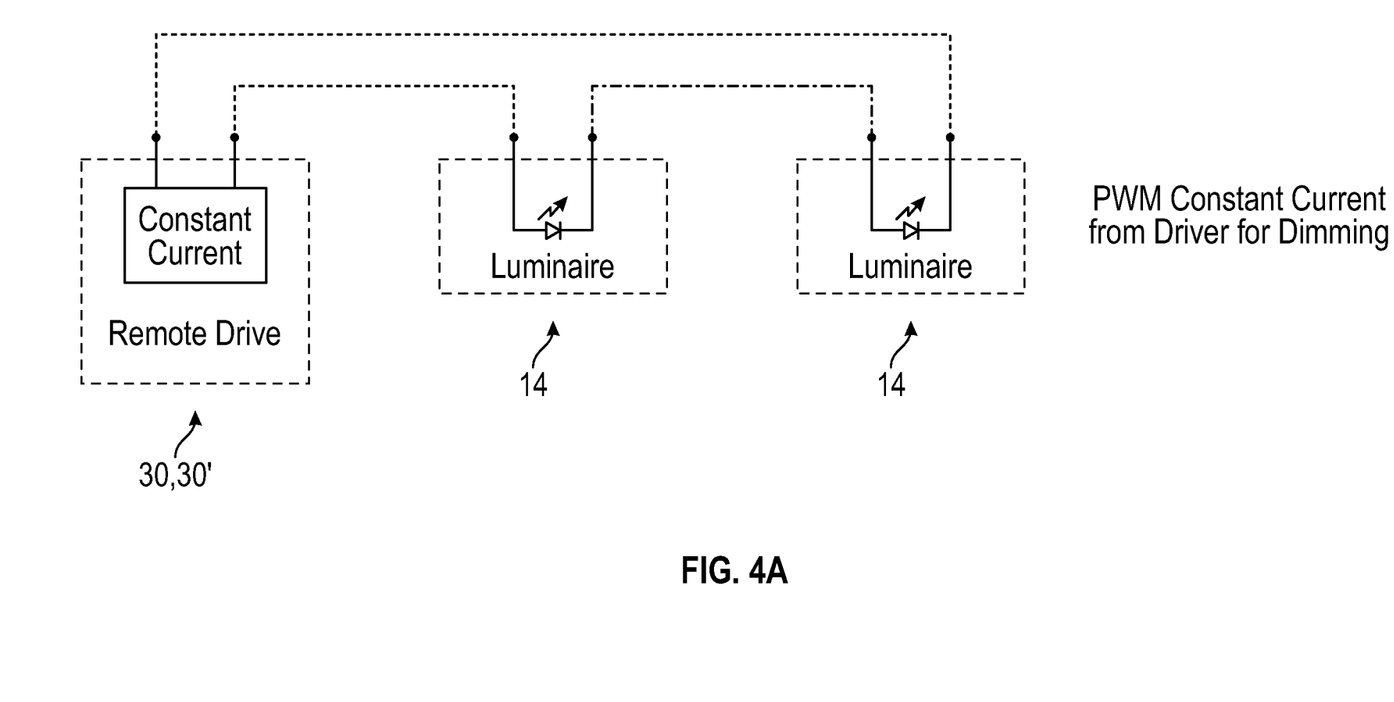
FIG. 4A is a schematic of a plurality of luminaires of FIGS. 1A, 1B, 2A, or 2B electrically coupled to one another and to the remote driver of either FIG. 1 or 2C.
Figure 4B:
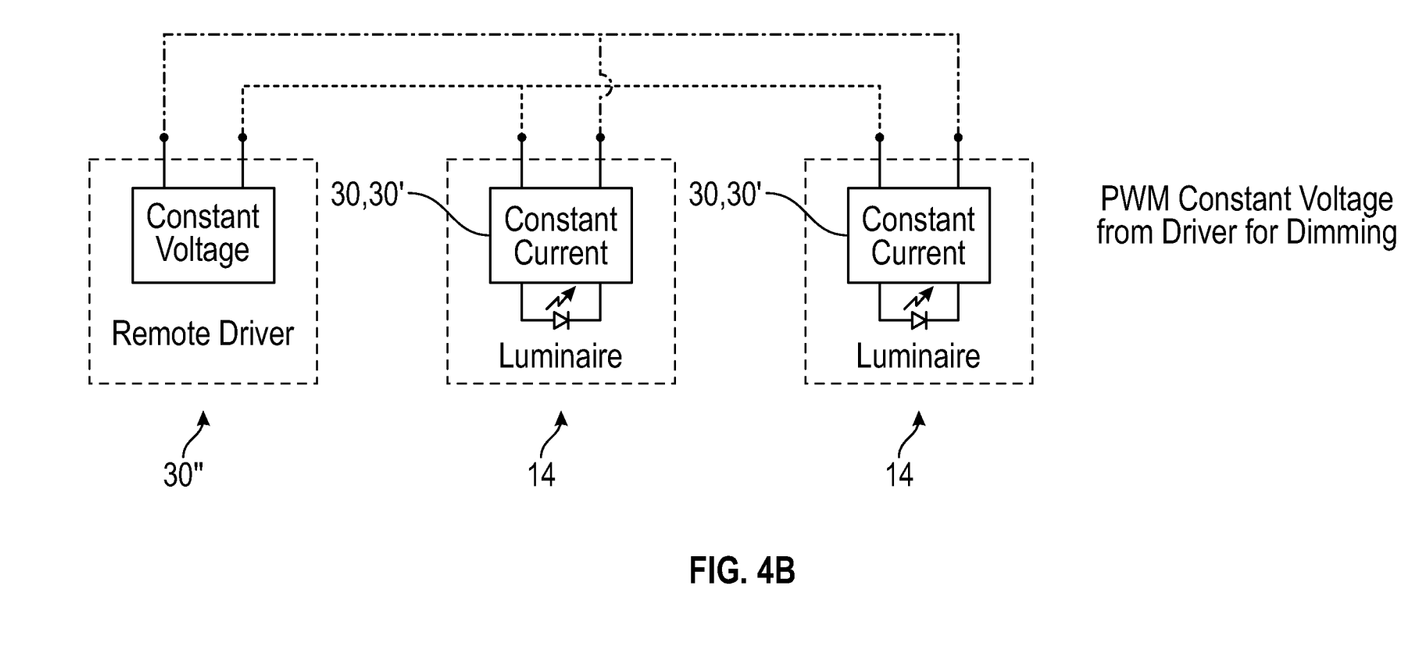
FIG. 4B is a schematic of a plurality of luminaires of FIGS. 1A, 1B, 2A, or 2B electrically coupled to one another and to a remote driver having yet another configuration.

FIG. 1A schematically illustrates a system 10 according to one including a luminaire 14, a switch 18, a power source 22 in electrical communication with the luminaire 14, a buck converter 26 in electrical communication with the power source 22, and a controller in the form of a remote driver 30 in communication with the power source 22. As shown in FIGS. 4A and 4B, the system 10 may include multiple luminaires 14 coupled to one another in parallel or in series, as will be discussed in greater detail below.

Figure 2A:
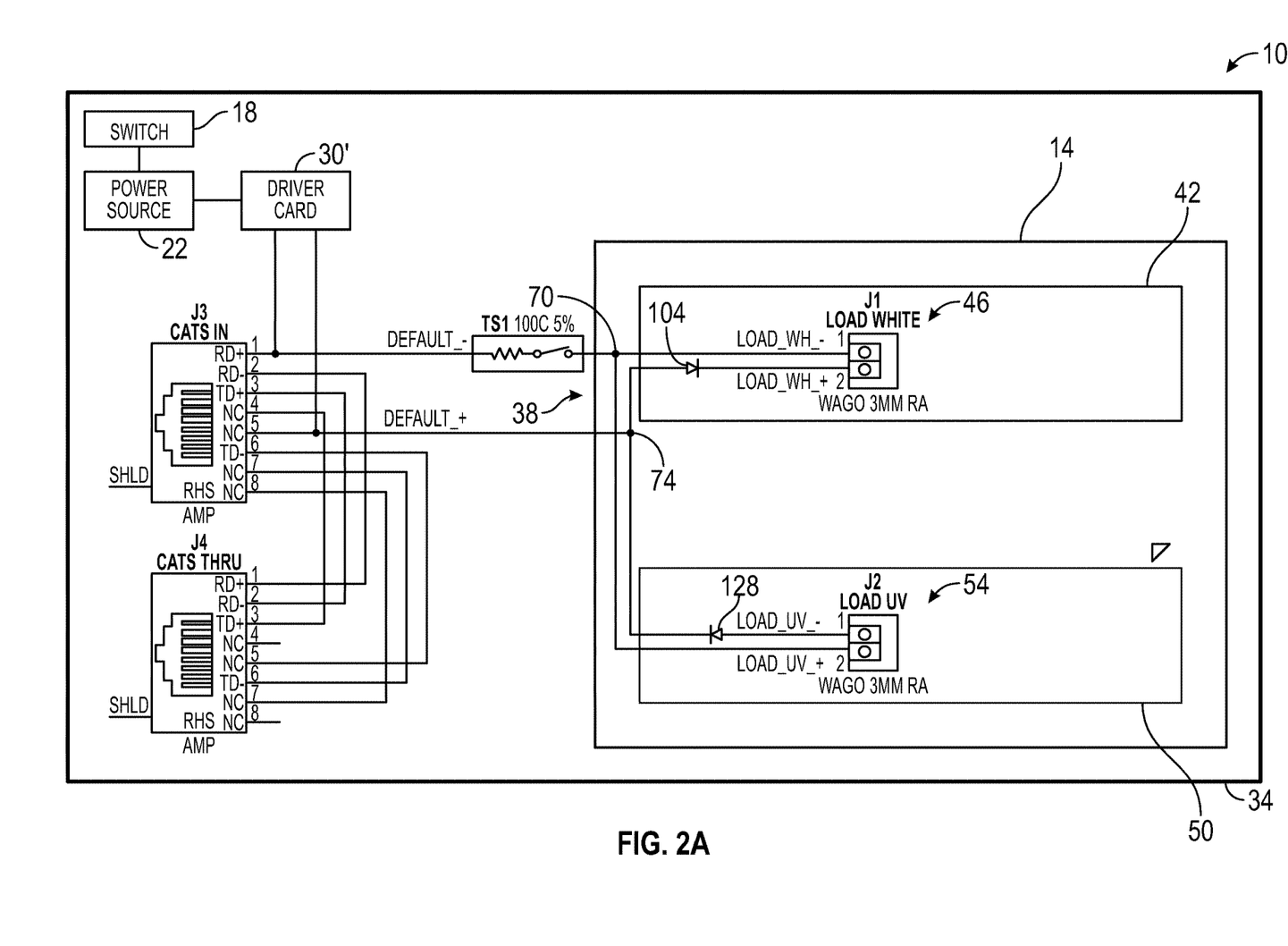
FIG. 2A a schematic of a system according to another embodiment including a remote driver having another configuration and including a luminaire having a first light source and a second light source.
Figure 2B:
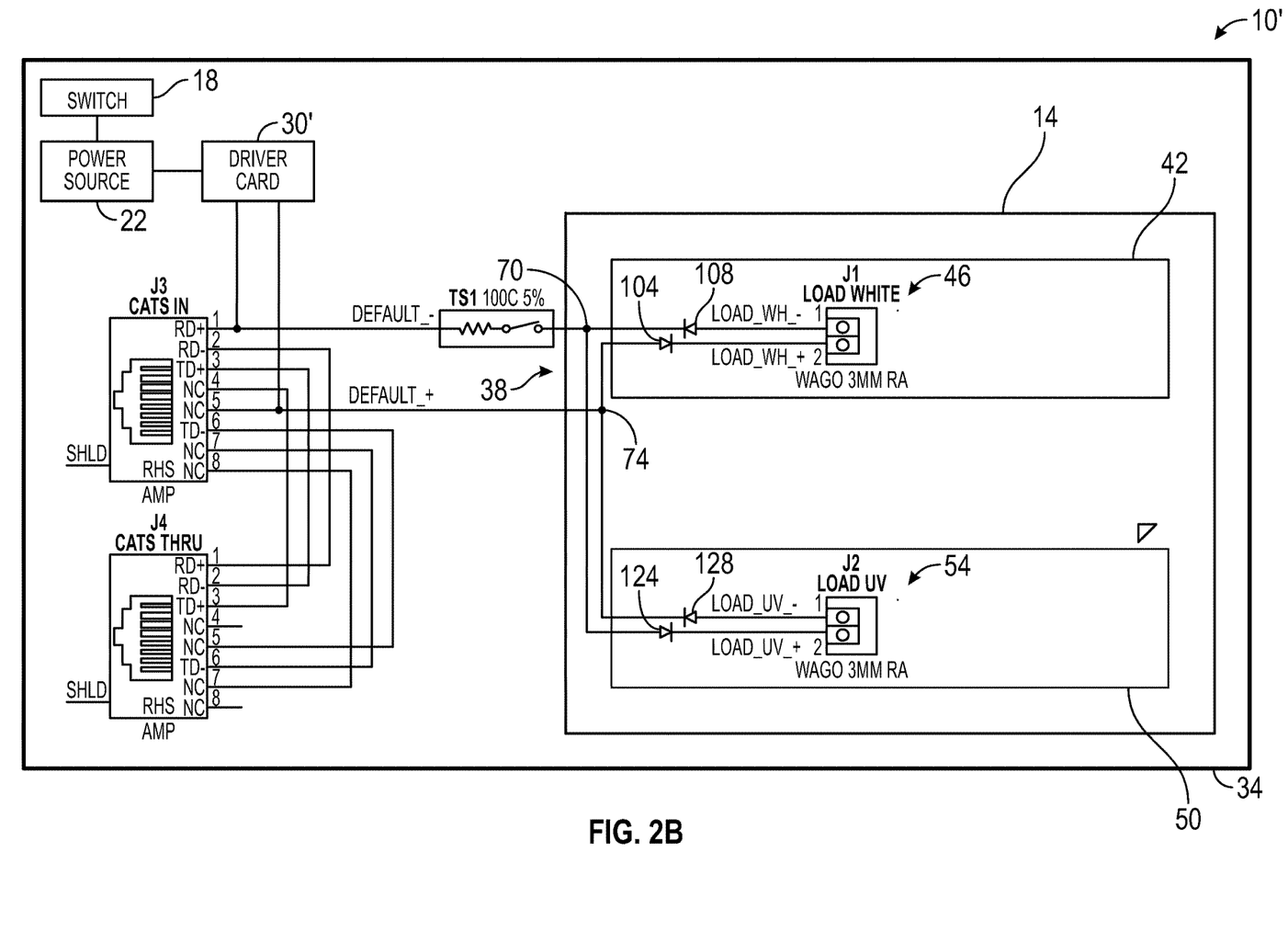
FIG. 2B a schematic of a system according to another embodiment including the remote driver of FIG. 2A and including a luminaire having a first light source and a second light source.
Figure 2C:
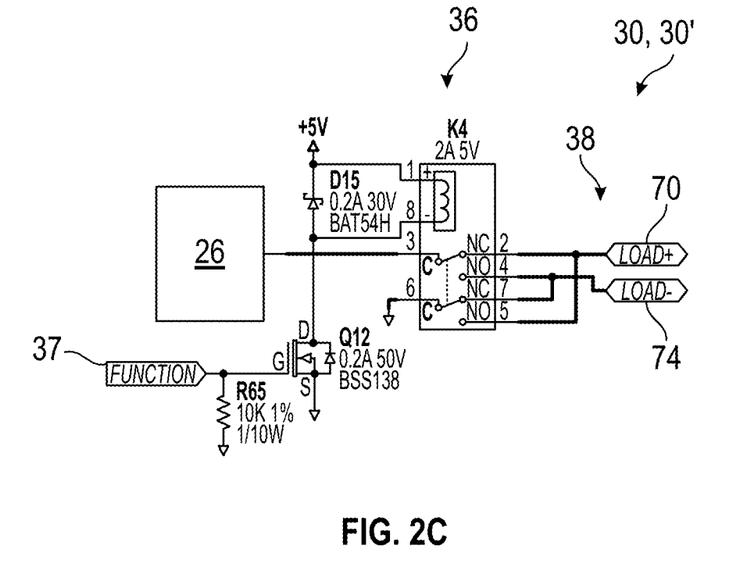
FIG. 2C is a schematic of a portion of the systems of FIGS. 2A and 2B.

FIG. 2A schematically illustrates a system 10' according to another embodiment including the luminaire 14, the power source 22 in electrical communication with the luminaire 14, and a controller in the form of a remote driver 30' in communication with the power source 22. The driver 30' is shown in greater detail in FIG. 2C, which illustrates the buck 26 as an element of the driver 30'. The power source 22 is electrical communication with the buck 26 of the driver 30'.

Regardless of embodiment, the luminaire 14 is designed to be positioned in an enclosed area 34 (e.g., a room). The illustrated power source 22 converts alternating (AC) power to direct current (DC) power (e.g., an AC/DC converters) and therefore provides DC power to the system 10, 10'. In other embodiments, the power source may be a DC power source, an AC power source, or another suitable power source.

The illustrated driver 30, 30' is used to switch the polarity of the power source 22. In the illustrated embodiments, the drivers 30, 30' may include a relay switch 36 (FIG. 2C) that switches the polarity of the power source 22 based on instructions received from a processor 37. In other embodiments, the polarity may be switched (e.g., switched between straight polarity and reverse polarity) in other suitable ways.

The switch 18 may be directly electrically coupled to the luminaire 14 (FIG. 1A) or may be in electrical communication with luminaire 14 via the power source 22 and driver 30' (FIG. 2A). In still some embodiments, the switch 18 may be incorporated into the luminaire 14. The switch 18 is configured to instruct the driver 30, 30' (via the relay 36 and the processor 37) to switch the polarity, as will be discussed in greater detail below. In some embodiments, the switch 18 may be a presence sensor configured to sense movement or infrared radiation to sense the presence of a person is in the enclosed area 34. In other embodiments, a physical switch 18 may be used in lieu of the sensor.

The luminaire 14 includes an input 38, a first circuit 42, a first light source 46, a second circuit 50, and a second light source 54. The first circuit 42 and the second circuit 50 are in simultaneous communication with the power source 22 via the input 38. In the illustrated embodiment, the input 38 includes a first input wire 70 and a second input wire 74. Moreover, the remote driver 30, 30' and the buck converter 26 are in electrical communication between the power source 22 and the first and the second circuits 42, 50 via the input 38. As noted above, the input 38 is capable of being driven in either a first polarity (e.g., straight polarity) or a second polarity (e.g., reverse polarity) reversed from the first polarity, via remote driver 30, 30' and the buck converter 26.

Figure 1B:
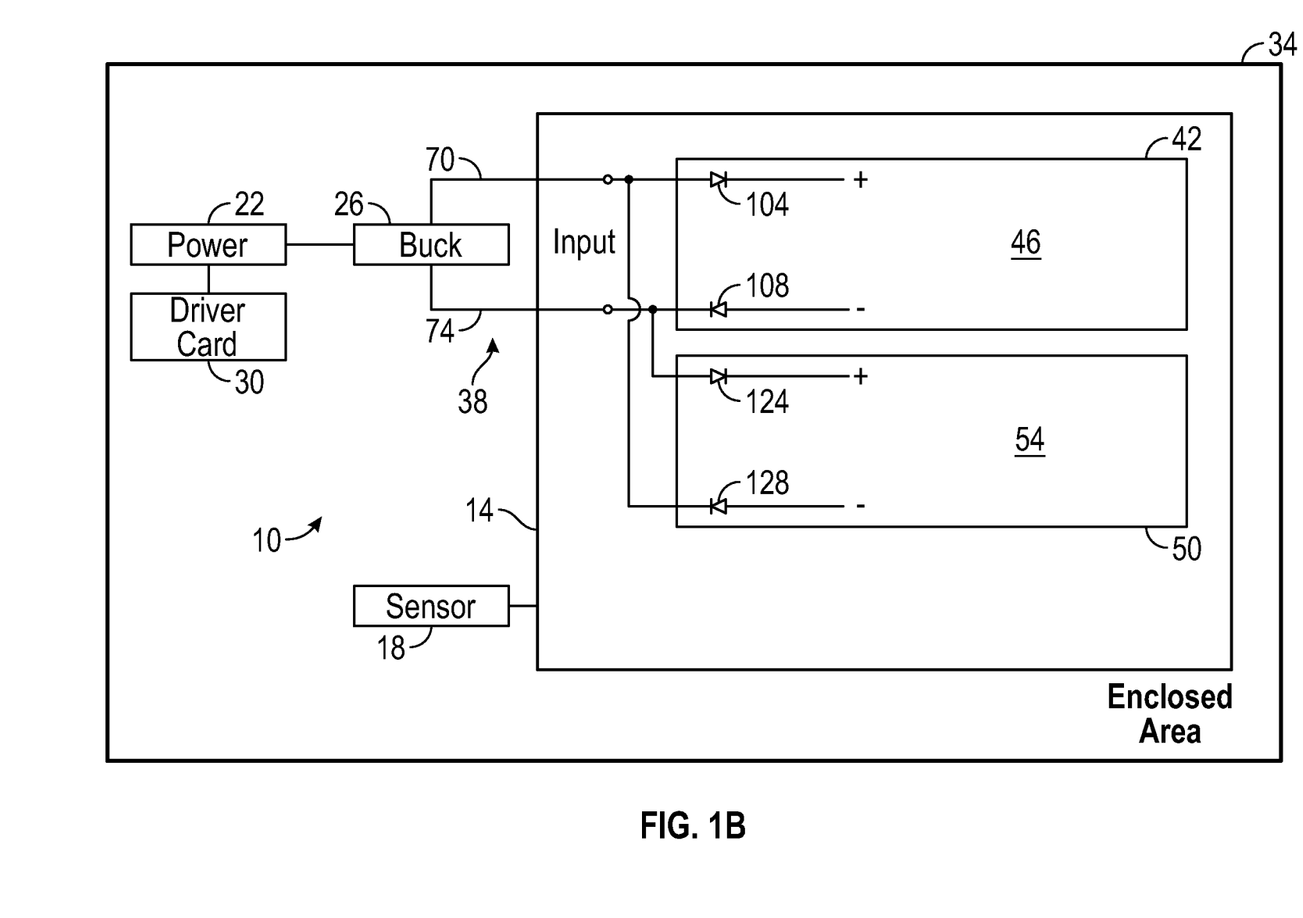
FIG. 1B a schematic of a system according to another embodiment including the remote driver of FIG. 1A and including a luminaire having a first light source and a second light source.

With respect to the embodiments of FIGS. 1A and 2A, the first circuit 42 includes a first steering diode 104 and the second circuit 50 includes a second steering diode 128. The steering diodes 104,128 in each of the first and second circuits 42, 50 limit current flow in one direction within the circuit. The first circuit 42 only has current when the power source 22 has the first polarity, and the second circuit 50 has current only when the power source has the second polarity. In an alternate embodiment, instead of stopping current flow in the first circuit when the second polarity is applied, the first circuit could allow some smaller amount of current to flow. The same applies to the second circuit when the first polarity is applied. Further, as shown in the alternative embodiments of FIGS. 1B and 2B, it is envisioned that the first circuit 42 may include two first steering diodes 104, 108, and the second circuit 50 may include two second steering diodes 124, 128.

Figure 3:
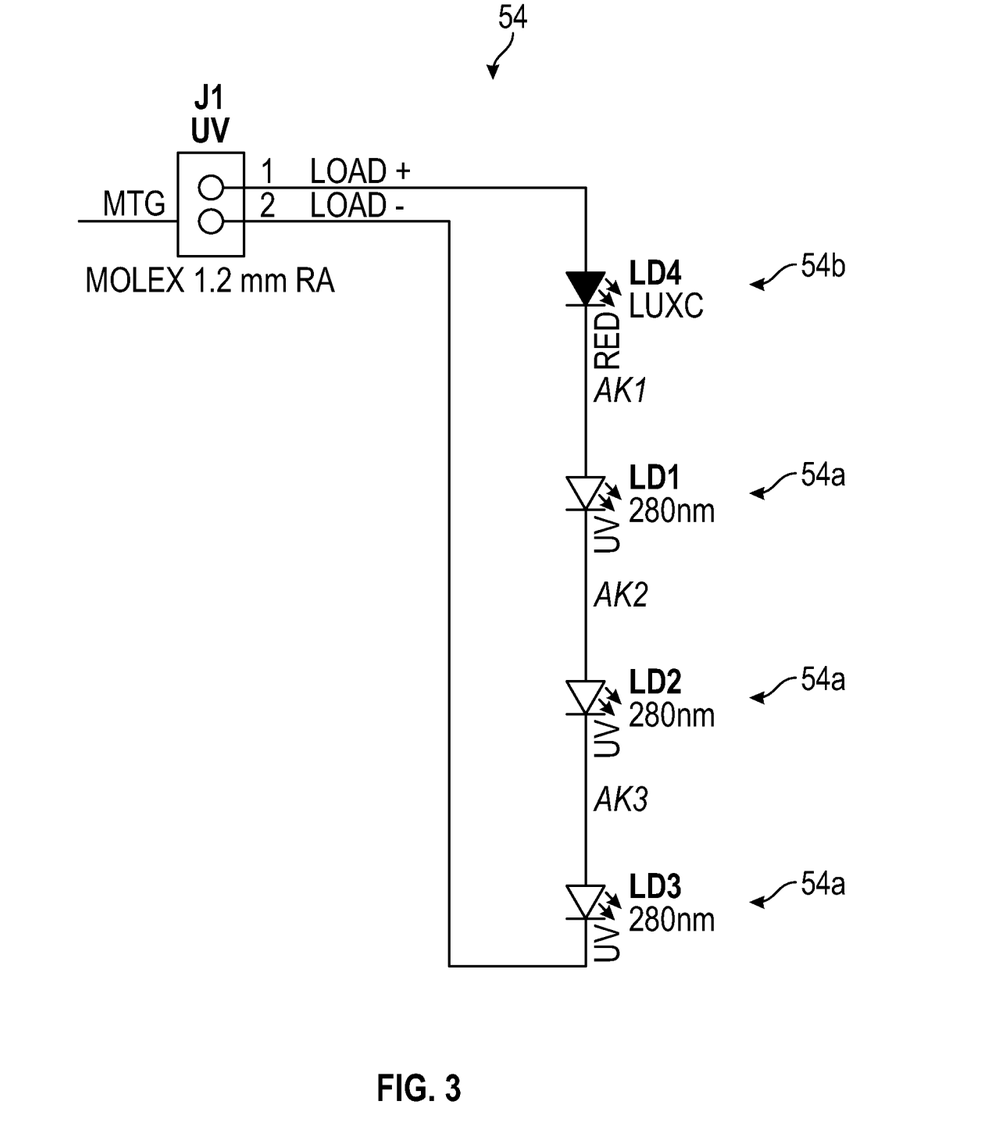
FIG. 3 is a schematic of the second light source of FIGS. 1A-2B.

In the illustrated embodiment, the first light source 46 includes light emitting diodes (LEDs) that emit visible light, such as white LEDs (e.g., LEDs having a wavelength of 390 nm-700 nm). In the illustrated embodiment, there are three LEDs but in other embodiments there may be any suitable number of visible light LEDs. When in use, the white LEDs emit white or visible light to illuminate the enclosed area 34. In the illustrated embodiment (as shown in FIG. 3), the second light source 54 includes LEDs 54a that emit non-visible or sanitizing light, such as ultraviolet (UV) LEDs (e.g., LEDs in the UV-C band having a wavelength of 100 nm-280 nm), and a LED 54b that emits colored or non-white visible light (e.g., a red LED). When in use, the UV LEDs 54a are used to sanitize the enclosed area 34 and the red LED 54b is used to alert persons that the UV LEDs are operating. In the illustrated embodiment, the LED 54b that emits non-white visible light is a blinking light. That is, the LED 54b emits non-white visible light in a repetitive pattern to alert persons that the UV LEDs are operating and emitting non-visible light. In other embodiments, the second light source 54 may include only UV LEDs that emit non-visible light. In still other embodiments, the second light source 54 may include only LEDs that emit visible light, such as one or more blue LEDs (e.g., LEDs having a wavelength of 450 nm-465 nm). The light sources 46, 54 may include LEDs having any suitable color combination, however. For example, the first light source 46 may include LEDs that are red and the second light source 54 may include LEDs that are blue. In another example, the first light source 46 may include LEDs that are white and the second light source 54 may include LEDs that are red or amber.

In the illustrated embodiments, each of the drivers 30, 30' is a constant current driver. Accordingly, the buck converter 26 is designed to receive voltage from the power source and regulate the current flow such that an operating current (e.g., 700 mA) is alternately delivered to the first and second circuits 42, 50 to selectively power the first and second light sources 46, 54 based on whether the remote driver 30, 30' is set to the first polarity or the second polarity. The buck converter 26 therefore regulates the current from the power source 22 to the first and second light sources 46, 54. Multiple luminaires 14 may be connected to one another in series and controlled by the constant current drive card 30, 30', as shown in FIG. 4A. The remote driver 30, 30' may also be configured to dim the first and second light sources 46, 54. That is, the driver 30, 30' will vary the current either by amplitude or duty cycle of a pulse width modulated (PWM) voltage, and the respective light source 46, 54 will dim directly from that signal.

In the illustrated embodiments, when the relay 36 of the remote driver 30, 30' is set (e.g., via the relay 36) to the first (e.g., straight) polarity, operating current from the power source 22 flows through the first circuit 42 and powers the first light source 46. That is, current flows in the direction of the first steering diode 104 of the first circuit 42 and is prevented from flowing against the direction of the second steering diode 128 of the second circuit 50. Accordingly, the first light source 46 is powered, but the second light source 54 is not powered. Accordingly, in the illustrated embodiment, because the first light source 46 is powered is powered, visible light (e.g., white light) illuminates the enclosed area 34, but the sanitizing light and non-white visible light are not emitted by the second light source 54.

When remote driver 30, 30' is set (e.g., via the relay 36) to the second (e.g., reverse) polarity, operating current from the power source 22 flows through the second circuit 50 and powers the second light source 54. That is, current flows in the direction of the second steering diodes 128 of the second circuit 50 and is prevented from flowing against the direction of the first steering diode 104 of the first circuit 42. Accordingly, the second light source 54 is powered, but the first light source 46 is not powered. In the illustrated embodiment, when the second light source 54 is powered sanitizing light (e.g., UV light) sanitizes the enclosed area 34 and non-white visible is also emitted to provide persons with a visual indication that the UV light is on. However, white visible light is not emitted by the first light source 46.

In other embodiments, each of the drivers 30" may be constant voltage drivers. In this case, the luminaire 14 also includes a constant current driver 30, 30', which regulates the current from the constant voltage remote driver 30" to the first and second light sources 46, 54. When a constant current driver 30", multiple luminaires 14 may be connected to one another in parallel, as shown in FIG. 4B. As noted above, however, each luminaire 14 also requires its own driver 30, 30'. The remote driver 30" may also be configured to dim the first and second light sources 46, 54. That is, the driver 30, 30' will vary the duty cycle of a PWM voltage, and the driver 30, 30' of the luminaire will convert the PWM voltage to a constant current to control or dim the respective light source 46, 54.

In the embodiments having the constant voltage driver 30", when the driver 30" is set to the first (e.g., straight) polarity, operating voltage flows to the driver 30, 30' of the luminaire 14. Accordingly, the driver 30, 30' of each luminaire 14 converts the operating voltage from the constant voltage driver 30" to the appropriate operating current and provides the appropriate operating current through the first circuit 42 to power the first light source 46. That is, as discussed above, current flows in the direction of the first steering diode 104 of the first circuit 42 and is prevented from flowing against the direction of the second steering diode 128 of the second circuit 50.

In the embodiments having the constant voltage driver 30", when the driver 30" is set to the second (e.g., reverse) polarity, operating voltage flows to the driver 30, 30' of the luminaire 14. Accordingly, the driver 30, 30' of each luminaire 14 converts the operating voltage from the constant voltage driver 30" to the appropriate operating current and provides the appropriate operating current through the second circuit 50 to power the second light source 54. That is, current flows in the direction of the second steering diode 128 of the second circuit 50 and is prevented from flowing against the direction of the first steering diode 104 of the first circuit 42.

In use, the luminaire 14 is designed to be positioned in the enclosed area 34 and electrically coupled to the switch 18 and the power source 22. When it is desired to have white visible light illuminate the enclosed area 34, the switch 18 is in a first operating state, which sets the driver 30, 30', 30" (via the relay 36 and the processor 37) to instruct the power source 22 to drive the luminaire in the first polarity such that the luminaire 14 emits white light via the first light source 46 to illuminate the enclosed area 34, as discussed above. In this configuration, the second light source 54 cannot illuminate because the second circuit 50 is blocked by the second steering diode 128. When it is desired to have sanitizing, non-white visible light, or both emitted the enclosed area 34, the switch 18 is in a second operating state, which causes the remote driver 30, 30', 30" (via the relay 36 and the processor 37) to reverse the polarity of the power source 22. As a result, current to the first light source 46 is blocked by the first and second steering diode 104 of the first circuit 42, and current to the second light source 54 is then initiated such that the luminaire 14 emits light via the second light source 54 to sanitize and/or emit a non-white visible light the enclosed area 34, as discussed above.

When the switch 18 is a sensor, the sensor 18 senses the presence (e.g., by movement or infrared radiation) of the person, which sets the driver 30, 30', 30" to instruct the power source 22 to drive the luminaire in the first polarity, as discussed above. When the person leaves the enclosed area 34, the sensor 18 senses the absence of the person (e.g., by lack of movement or infrared radiation), and the remote driver 30 reverses polarity of the power source 22, as discussed above. If a person subsequently enters the enclosed area 34, the sensor 18 senses the presence of the person and the remote driver 30 directs the power source 22 to return to first polarity to block the second light source 54 and power the first light source 46.

The luminaire 14 of the present disclosure uses two light sources 46, 54 (e.g., the white LEDs and UV LEDs) with a single power source 22 (i.e., hot and neutral wires) and single driver 30, which is advantageous over devices in which two light sources require separate power sources, switches, data cabling, and/or drivers.

Additionally, in the embodiments in which the second light source is a sanitizing light source, because the first and second light sources 46, 54 cannot operate simultaneously, the likelihood of a person being exposed to UV light is reduced. Also, when the white light is visible in an enclosed room, a person can know that the enclosed area is not being sanitized and will not be exposed to the UV LEDs.

Although the disclosure has been described in detail with reference to certain preferred aspects, variations and modifications exist within the scope and spirit of one or more independent aspects of the disclosure as described. Various features and advantages of the disclosure are set forth in the following claims.

What is claimed is:

1. A luminaire configured to communicate with a power source, the luminaire comprising:
an input capable of being driven in a first polarity and a second polarity reversed from the first polarity, the input comprising a first input supply line and a second input supply line, each of the first input supply line and the second input supply line configured to communicate with the power source;
a first circuit coupled to the first input supply line and the second input supply line, the first circuit including a first current steering diode and a first light source, the first light source adapted to generate visible light within a first wavelength range at a first intensity when the input is driven in the first polarity and adapted to generate visible light within the first wavelength range at a second intensity less than the first intensity when the input is driven in the second polarity; and
a second circuit coupled to the first input supply line and the second input supply line, the second circuit including a second steering diode and a second light source, the second light source adapted to generate light within a second wavelength range at a third intensity when the input is driven in the second polarity and adapted to generate light within the second wavelength range at a fourth intensity less than the third intensity when the input is driven in the first polarity, the second wavelength range being different than the first wavelength range, wherein
the first current steering diode is in electrical communication with the first input supply line to provide current to the first light source when the input has the first polarity and inhibit current to the first light source when the input has the second polarity, the first circuit configured to receive current only when the input is driven in the first polarity;
the second current steering diode is in electrical communication with the first input supply line to provide current to the second light source when the input has the second polarity and inhibit current to the second light source when the input has the first polarity, the second circuit configured to receive current only when the input is driven in the second polarity; and
the first input supply line and the second input supply line configured to simultaneously supply voltage from the power source to the first circuit and the second circuit.

2. The luminaire of claim 1, wherein the first light source includes one or more white light emitting diodes and the second light source includes one or more ultraviolet light emitting diodes.

3. The luminaire of claim 2, wherein the second light source further includes one or more colored LEDs.

4. The luminaire of claim 1, wherein the second and fourth intensities are substantially zero.

5. The luminaire of claim 1, wherein the second light source is adapted to generate non-visible light.

6. The luminaire of claim 1, wherein the second light source is adapted to generate visible light.

7. The luminaire of claim 1, wherein the second light source is adapted to generate non-visible light and visible light.

8. The luminaire of claim 1, wherein
the first circuit includes a positive terminal in electrical communication with the first supply line and the first light source and a negative terminal in electrical communication with the second supply line and the first light source,
the second circuit includes a positive terminal in electrical communication with the second supply line and the second light source and a negative terminal in electrical communication with the first supply line and the second light source, and
the first input line is between the positive terminal of first circuit and the negative terminal of the second circuit.

9. The luminaire of claim 8, wherein the first steering diode is in electrical communication with the positive terminal of the first circuit, and the second steering diode is in electrical communication with a negative terminal of the second circuit.

10. The luminaire of claim 9, wherein the first steering diode is forward biased from the first input line to the positive terminal of the first circuit and the second steering diode is forward biased from the negative terminal of the second circuit to the second input line.

11. The luminaire of claim 1, further comprising a buck converter in electrical communication with the power source, the first circuit, and the second circuit, the buck converter configured to receive voltage from the power source and regulate a current flow to an operating current.

12. A system comprising:
a power source;
a controller coupled to the power source and capable of switching a polarity of the power source from a first polarity to a second polarity reversed from the first polarity; and
an input in communication with the power source via the controller, the input comprising a first input supply line and a second input supply line;
a first circuit coupled to the first input supply line and the second input supply line, the first circuit including a first current steering diode and a first light source, the first light source adapted to generate visible light within a first wavelength range at a first intensity when the input is driven in the first polarity and adapted to generate visible light within the first wavelength range at a second intensity less than the first intensity when the input is driven in the second polarity; and
a second circuit coupled to the first input supply line and the second input supply line, the second circuit including a second steering diode and a second light source, the second light source adapted to generate light within a second wavelength range at a third intensity when the input is driven in the second polarity and adapted to generate light within the second wavelength range at a fourth intensity less than the third intensity when the input is driven in the first polarity, the second wavelength range being different than the first wavelength range, wherein
the first current steering diode in electrical communication with the first input supply line to provide current to the first light source when the input has the first polarity and inhibit current to the first light source when the input has the second polarity, the first circuit configured to receive current only when the input is driven in the first polarity;
the second current steering diode in electrical communication with the first input supply line to provide current to the second light source when the input has the second polarity and inhibit current to the second light source when the input has the first polarity, the second circuit configured to receive current only when the input is driven in the second polarity; and the first input supply line and the second input supply line simultaneously supply voltage from the power source to the first circuit and the second circuit via the controller.

13. The system of claim 12, further comprising a sensor in communication with the controller, the controller receiving information from the presence sensor to control the polarity of the power source.

14. The system of claim 12, wherein the first light source includes one or more white light emitting diodes and the second light source includes one or more ultraviolet light emitting diodes.

15. The system of claim 14, wherein the second light source further includes one or more colored LEDs.

16. The system of claim 12, wherein the second and fourth intensities are substantially zero.

17. The system of claim 12, wherein the controller is a constant current driver.

18. The system of claim 12, wherein the controller is a constant voltage driver and the luminaire further includes a constant current driver in communication with the constant voltage driver and the input.

19. The system of claim 12, wherein a first light source is adapted to generate visible light within the first wavelength range at a fifth intensity when the input is driven in the first polarity, the fifth intensity being less than the first intensity but greater than the second intensity.

20. A system comprising:
a power source;
a controller coupled to the power source and capable of switching a polarity of the power source from a first polarity to a second polarity reversed from the first polarity, the controller being a constant current driver; and
a plurality of luminaires electrically connected in series, each luminaire including
an input in communication with the power source via the controller, the input comprising a first input supply line and a second input supply line;
a first circuit coupled to the first input supply line and the second input supply line, the first circuit including a first current steering diode and a first light source, the first light source adapted to generate visible light within a first wavelength range at a first intensity when the input is driven in the first polarity and adapted to generate visible light within the first wavelength range at a second intensity less than the first intensity when the input is driven in the second polarity; and
a second circuit coupled to the first input supply line and the second input supply line, the second circuit including a second steering diode and a second light source, the second light source adapted to generate light within a second wavelength range at a third intensity when the input is driven in the second polarity and adapted to generate light within the second wavelength range at a fourth intensity less than the third intensity when the input is driven in the first polarity, the second wavelength range being different than the first wavelength range, wherein
the first current steering diode in electrical communication with the first input supply line to provide current to the first light source when the input has the first polarity and inhibit current to the first light source when the input has the second polarity, the first circuit configured to receive current only when the input is driven in the first polarity;
the second current steering diode in electrical communication with the first input supply line to provide current to the second light source when the input has the second polarity and inhibit current to the second light source when the input has the first polarity, the second circuit configured to receive current only when the input is driven in the second polarity;
the first input supply line and the second input supply line simultaneously supply voltage from the power source to the first circuit and the second circuit via the controller.

21. The system of claim 20, further comprising a processor and a relay switch, the relay switch configured to switch the polarity of the power source from the first polarity to the second polarity reversed from the first polarity based on instructions from the processor.

* * * * *